US006562004B1

(12) United States Patent
Doukas et al.

(10) Patent No.: US 6,562,004 B1
(45) Date of Patent: May 13, 2003

(54) TRANSDERMAL DELIVERY

(75) Inventors: Apostolos Doukas, Belmont, MA (US); Shun Kwan Lee, Boston, MA (US); Thomas J. Flotte, Boston, MA (US)

(73) Assignee: The Massachusetts General Hospital, Boston, MA (US)

( * ) Notice: Subject to any disclaimer, the term of this patent is extended or adjusted under 35 U.S.C. 154(b) by 275 days.

(21) Appl. No.: 09/587,333

(22) Filed: Jun. 5, 2000

(51) Int. Cl.$^7$ .............................................. A61M 37/00
(52) U.S. Cl. ........................................ 604/145; 604/140
(58) Field of Search ......................... 604/68–69, 140, 604/141, 131, 143, 145, 147

(56) References Cited

U.S. PATENT DOCUMENTS

| | | | |
|---|---|---|---|
| 4,767,808 A | 8/1988 | Kydonieus et al. ............ 524/98 |
| 4,787,888 A | 11/1988 | Fox | |
| RE34,089 E | 10/1992 | Kydonieus et al. .......... 424/449 |
| 5,421,816 A | 6/1995 | Lipkovker .................... 604/20 |
| 5,468,501 A | 11/1995 | Kydonieus et al. .......... 424/443 |
| 5,611,793 A | 3/1997 | Wilson et al. .................. 606/2 |
| 5,614,502 A | 3/1997 | Flotte et al. .................. 514/34 |
| 5,656,016 A | 8/1997 | Ogden ............................ 601/2 |
| 5,658,247 A | 8/1997 | Henley | |
| 5,686,099 A | 11/1997 | Sablotsky et al. ........... 424/449 |
| 5,713,845 A | 2/1998 | Tankovich .................... 604/20 |
| 5,947,928 A | * 9/1999 | Muller ........................ 604/140 |
| 6,096,000 A | 8/2000 | Tachibana et al. | |

FOREIGN PATENT DOCUMENTS

| | | | |
|---|---|---|---|
| EP | WO 98/23325 | 4/1998 | ............ A61N/1/30 |
| WO | WO 98/57695 | 12/1998 | .......... A61M/37/00 |

OTHER PUBLICATIONS

Lee et al., "Photomechanical Transcutaneous Delivery Of Macromolecules" 111:925–929, *J. of Investigative Dermatology* 1998.
Lee et al., "Topical Drug Delivery in Humans with a Single Photomechanical Wave", *Pharmaceutical Research*, 16;1717–1721, 1999.
Kodama et al., "Innovative Technology for Tissue Disruption by Explosive–Induced Shock Waves", *Ultrasound in Med. & Biol.* 24:1459–1466 (1998).

* cited by examiner

*Primary Examiner*—Manuel Mendez
*Assistant Examiner*—Michael M Thompson
(74) *Attorney, Agent, or Firm*—Fish & Richardson P.C.

(57) ABSTRACT

A device for transdermal delivery of a composition includes a housing partitioned into a delivery chamber arranged to contain the composition and a detonation chamber mechanically coupled to the delivery chamber. The detonation chamber is intended to contain an energetic material producing an impulse transient in response to a detonating stimulus. The housing is coupled to an energy coupling element, or detonator, for communicating energy provided by an external energy source into the detonating stimulus in the detonation chamber. The detonator can detonate the energetic material by causing an electrical discharge or spark within the detonation chamber. The detonator can be a piezoelectric film in electrical communication with the energetic material.

29 Claims, 8 Drawing Sheets

TRANSDERMAL DELIVERY

FIELD OF THE INVENTION

This invention relates to transdermal delivery of compositions.

BACKGROUND OF THE INVENTION

Despite its often placid appearance, the environment we live in is one that is unrelentingly hostile to human life. In addition to being contaminated by pathogenic microorganisms, the environment is filled with compositions that, if permitted to interact with the internal structures of the human body, would seriously interfere with the many chemical reactions required to sustain life. An important function of the human skin is to limit the entry of undesirable compositions into the human body.

The effectiveness of the skin at excluding harmful compositions from the interior of the human body allows us to freely apply lotions, cosmetics, topical ointments, and insect repellents on the skin with little concern about the toxicity of those compositions. However, this same effectiveness sharply curtails our ability to deliver medicines intended for systemic distribution through the skin and into the bloodstream.

There exist devices that passively deliver compositions through the skin. Because of their reliance on diffusion, only very small molecules can readily be delivered using such passive devices. In addition, the time required to deliver the composition is limited by the rate of diffusion and by the concentration gradient.

There also exist devices that actively deliver compositions through the skin. Such active transdermal delivery devices typically rely on iontophoresis, in which a voltage drives charged molecules of the composition through the skin, phonophoresis, in which ultrasonic waves exert a mechanical force that drives the composition through the skin, and photophoresis, in which a laser assists in the delivery of a composition through the skin. The requirement of complex devices in the latter two cases and the need to ionize the composition in the former case limits the widespread use of these devices.

SUMMARY OF THE INVENTION

The invention is based on the discovery that an explosion can be used to generate a high pressure impulse transient or stress wave that is effective to temporarily enhance the permeability of the skin. The invention provides transdermal delivery devices and methods for safely and efficiently delivering a composition through the skin. These devices include an explosive material that is detonated to generate impulse transients that permeabilize the skin and to thereby allow the composition to diffuse passively through the permeabilized skin. The invention also provides devices and methods for harnessing the forces generated by these impulse transients to actively drive the composition through the temporarily permeabilized skin.

Each impulse transient is a broad-band compressive wave having a rise time of approximately 1 nanosecond and a peak pressure approximately 600 bar less than that overpressure that would cause skin damage. The impulse transient typically has a duration between 100 nanoseconds and 1100 nanoseconds, e.g., 500–700 nanoseconds. The impulse transient is typically generated by detonating an energetic material in the device or by causing an explosive reaction in the device.

A transdermal delivery device according to the invention includes a housing having a partition that divides the housing into a detonation chamber for containing an energetic, or explosive material and a delivery chamber, for containing a composition to be delivered across a patient's skin. The detonation chamber is mechanically coupled to the delivery chamber so that an impulse transient generated within the detonation chamber propagates into and through the delivery chamber and into the patient's skin. The device further includes an energy coupling element for transforming energy provided by an external source into a detonating stimulus for detonating the energetic material in the detonation chamber.

In one embodiment, the transdermal delivery device includes a second partition across the housing so that the housing also includes an expansion chamber that is in mechanical communication with both the detonation chamber and the delivery chamber. The expansion chamber contains an expansion material that expands in volume in response to an impulse transient. Preferably, the expansion chamber is disposed between the detonation chamber and the delivery chamber.

The energy coupling element can be a piezoelectric film in electrical communication with the energetic material in the detonation chamber. Another convenient energy coupling element for the transdermal delivery device is a DC voltage source in electrical communication with the energetic material in the detonation chamber.

The invention also includes a method of manufacturing a transdermal delivery device by dividing a housing into a delivery chamber and a detonation chamber separate from the delivery chamber. An energetic material is then placed in the detonation chamber and a composition to be delivered transdermally can be placed in the delivery chamber. An energy coupling element, or detonator, is then coupled to the energetic material within the detonation chamber for transforming energy provided by an external energy source into a detonating stimulus.

Preferably, the energy coupling element is a piezoelectric material on the housing, the piezoelectric material being in electrical communication with the energetic material. However, the energy coupling element can also include electrodes in communication with the energetic material. The electrodes can be attached to a voltage source when the device is to be detonated.

The method can also include dividing the housing into an expansion chamber in mechanical communication with both the delivery chamber and the detonation chamber. The expansion chamber is then filled with an expansion material selected to expand in volume in response to an impulse transient generated by the energetic material.

A method for delivering a composition across the skin, in accord with the principles of the invention, includes placing, on the skin, a housing having a detonation chamber mechanically coupled to a delivery chamber containing the composition. With the housing on the skin, an energetic material disposed in a detonation chamber is then detonated. This generates an impulse transient that propagates through the delivery chamber and permeabilizes the skin.

In one embodiment, the method also includes providing an expansion chamber in mechanical communication with the detonation chamber and the delivery chamber. This expansion chamber contains an expansion material selected to expand in volume in response to the impulse transient generated within the detonation chamber.

To detonate the energetic material, one deforms a piezoelectric film in electrical communication with the energetic material. This generates an electrical discharge to detonate the energetic material. Alternatively, the energetic material can be detonated by applying a voltage across first and second electrodes in electrical communication with the energetic material.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

A transdermal delivery device according to the invention enables the rapid delivery of a composition through the skin by harnessing the energy from an explosion to permeabilize the skin. The explosion is detonated without the intervention of complex devices such as lasers or ultrasound generators. This greatly simplifies the administration of compositions.

In addition, the transdermal delivery device harnesses the force of the explosion to propel the composition across the skin. As a result, considerably greater quantities of the composition can be transported across the skin during the interval in which the skin is rendered permeable by the impulse transient generated by the explosion.

Other features and advantages of the invention will be apparent from the following detailed description, and from the claims.

DETAILED DESCRIPTION

The invention provides transdermal delivery devices and methods for delivering compositions through the skin by harnessing the energy generated from an explosion to permeabilize the skin, and, optionally, to propel the composition through the permeabilized skin. The composition can include one or more constituents dissolved or suspended in a coupling medium.

A transdermal delivery device incorporating principles of the invention exploits the fact that an impulse transient incident on the skin temporarily enhances its permeability, thereby creating a window of opportunity for the transdermal delivery of the composition. During this window of opportunity, hereafter referred to as a "delivery interval," the transdermal delivery device either allows the composition to flow passively into and through the permeabilized skin or harnesses the forces generated by an explosion to actively propel the composition through the temporarily permeabilized skin.

Structure of the Transdermal Delivery Device

Figure 1:
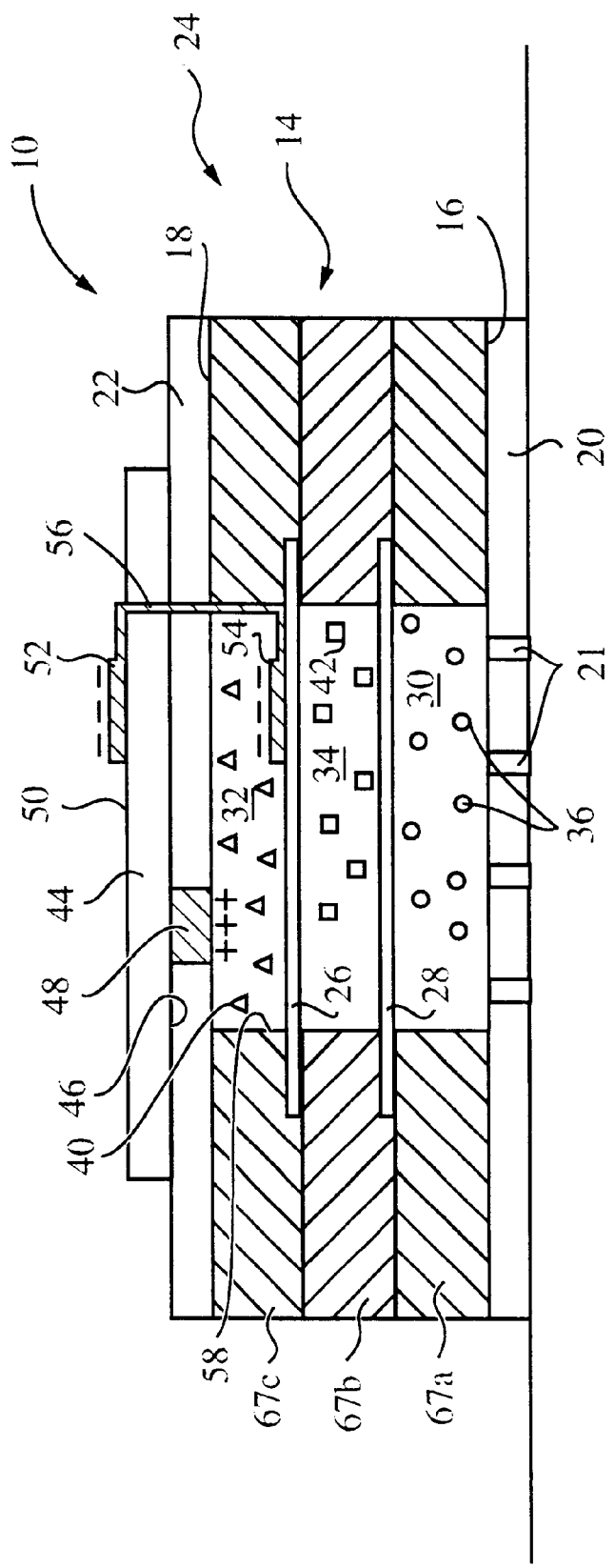
FIG. 1 is a schematic cross-section of a transdermal delivery device having a piezoelectric film.
Figure 2A:
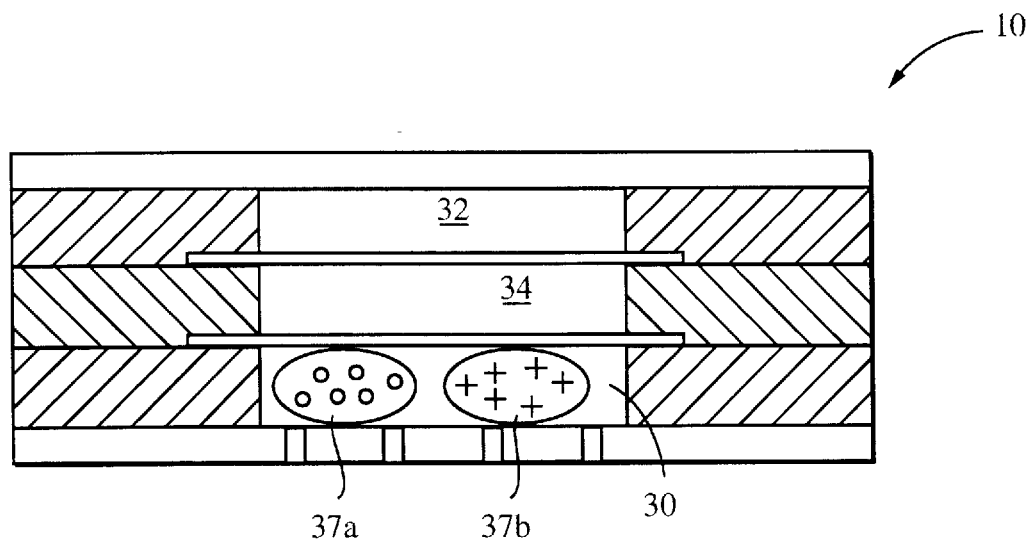
FIG. 2A is a schematic cross-section of a transdermal delivery device in which the composition to be delivered is separated into two compartments.
Figure 2B:
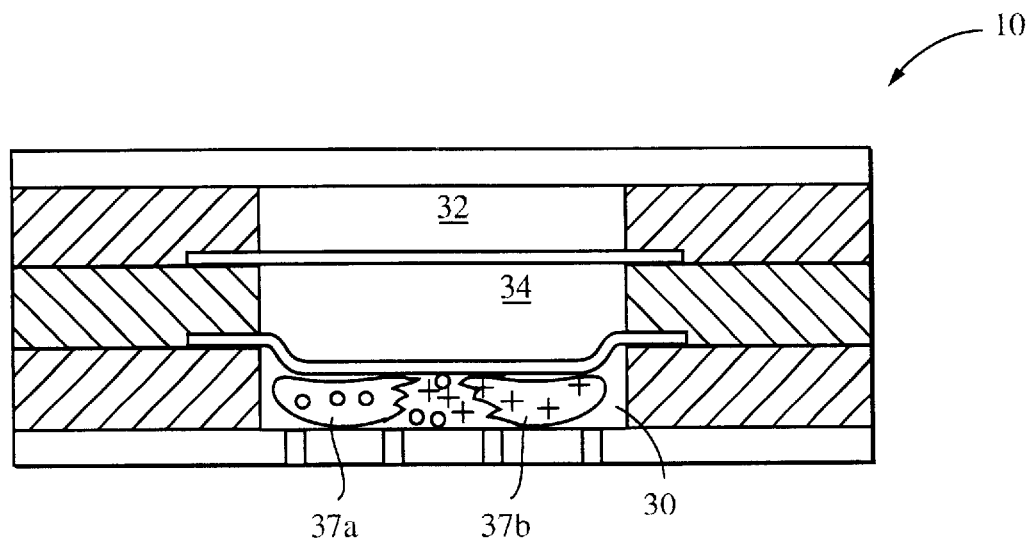
FIG. 2B is a schematic cross-section of the transdermal delivery device of FIG. 2A in which the compartments have been ruptured.

Referring to FIG. 1, a transdermal delivery device 10 includes a vertical wall 14 having a distal rim 16 and a proximal rim 18. A distal cap 20 and a proximal cap 22 engage, respectively, the distal rim 16 and the proximal rim 18 of the vertical wall 14. Together, the vertical wall 14, the distal cap 20, and the proximal cap 22 form a housing 24 enclosing an interior volume. A proximal dividing membrane 26 and a distal dividing membrane 28 span the interior volume enclosed by the housing 24, thereby partitioning the interior volume into a delivery chamber 30, a detonation chamber 32, and an expansion chamber 34 disposed between the delivery chamber 30 and the detonation chamber 32.

The vertical wall 14 preferably has sufficient flexibility to conform to the shape of the body surface and sufficient rigidity to withstand the forces generated by an explosion in the detonation chamber 32. Typically, the peak pressure generated in the detonation chamber 32 is on the order of 600–1000 bar. However, higher peak pressures, such as 900 bar to 2000 bar are possible depending on the nature of the composition to be delivered, provided that the peak pressure is less than that which would cause permanent skin damage. In addition, lower peak pressures, for example 400–600 bar, can be generated, with the lower bound being the peak pressure that fails to sufficiently permeabilize the skin. A suitable vertical wall 14 can be fabricated from stacked rubber washers or similar annular structures (e.g., plastic washers). The dimensions of the interior volume are tailored for the particular application. For example, a large dosage can require a large footprint on the skin and will therefore require the vertical wall 14 to enclose a large area. The height of the vertical wall 14 likewise depends on the specific application. For example, if rapid delivery is required, the expansion chamber 34 may need more volume, in which case the vertical wall 14 will need to be high enough to accommodate an expansion chamber 34 having the requisite volume. Similarly, depending on the nature of the explosive material, the detonation chamber 32 may need more volume to accommodate gaseous byproducts of the explosion. For most applications, the vertical wall 14 is no more than about 5 mm high, but can vary from 2 mm to 10 mm.

It is desirable that the impulse transient generated in the detonation chamber 32 be transmitted into the expansion chamber 34. For this reason, the proximal dividing membrane 26 separating the detonation chamber 32 from the expansion chamber 34 is selected to provide an impedance match between the wave propagation medium in the detonation chamber 32 and that in the expansion chamber 34, thereby minimizing any reflections at the boundary between the two chambers. The impedance required of the proximal dividing membrane 26 depends on both the material properties of the wave propagation medium in the detonation chamber 32 and that in the expansion chamber 34. However, if the proximal dividing membrane 26 is sufficiently thin relative to the spatial extent (typically 1.5 mm) of the pressure wave, the effect of the proximal dividing membrane 26 will be minimal. In one embodiment, the proximal dividing membrane 26 is a polyethylene membrane or a mylar membrane sandwiched between a pair of rubber washers or similar annular structures.

The distal dividing membrane 28 separating the expansion chamber 34 from the delivery chamber 30 is preferably impermeable. This will ensure that forces generated by expansion of the material within the expansion chamber 34 are not dissipated by diffusion or transport through the distal dividing membrane 28. In addition, the distal dividing membrane 28 is sufficiently flexible so that forces generated by expansion of material within the expansion chamber 34 can force the distal dividing membrane 28 into the delivery chamber 30, thereby reducing the volume of the delivery chamber 30 and providing motive force for transdermal delivery of its contents. In one embodiment, the distal dividing membrane 28 is a polyethylene membrane or a mylar membrane sandwiched between a pair of rubber washers or similar annular structures.

The distal cap 20 is preferably flexible enough to conform to the portion of the body on which the transdermal delivery device 10 is to be applied. In addition, the distal cap 20 must be sufficiently permeable so that the rapid decrease in volume of the delivery chamber 30 propels the contents of the delivery chamber 30 through the distal cap 20 and into the skin, rather than rupturing the device. The distal cap 20 can be permeable at the molecular level. However, the distal cap 20 can also include perforations 21 to facilitate the exit of the contents of the delivery chamber 30. These perforations 21 can be covered with a plastic film adhering to the distal cap 20 that is peeled off before using the device 10.

The proximal cap 22 is selected to be sufficiently rigid to avoid dissipating energy through deformation when an explosion occurs in the detonation chamber. The proximal cap 22 must, however, also be sufficiently flexible to conform to the shape of the body part to which the transdermal delivery device 10 is applied. Both the dimensions of the proximal cap 22 and the materials of which it is made can be altered for particular applications so long as the foregoing constraints are met. For example, virtually any material can form a rigid proximal cap 22 if it is made sufficiently thick. Similarly, if the explosive force is not excessive, materials and dimensions that would otherwise be unusable will become usable. The extent to which the proximal cap 22 must be flexible depends on the radius of curvature of the body part to which the transdermal delivery device 10 is to be applied, the cross-sectional area of the transdermal delivery device 10, and the height of the vertical wall 14.

Contents of the Structure: Composition

When configured for operation, the delivery chamber 30 contains a composition 36 to be delivered transdermally. The composition 36 can include one or more constituents in a coupling medium. Typical coupling media for use in the composition 36 include: aqueous media, such as water in solution with a surfactant; or oil-based media, such as castor oil. The addition of a surfactant is particularly advantageous because a surfactant tends to extend the delivery interval. Examples of suitable surfactants include sodium lauryl sulfate, benzalkonium chloride, and cocoamidopropyl betaine. The choice of a surfactant and the concentration of surfactant depend on the irritability of the person's skin and the desired delivery interval. This in turn will depend on the composition 36 to be delivered and the rate at which it can be delivered.

Constituents that can be included in the composition 36 include: large protein molecules such as insulin, polypeptides, antibodies, or antigens for allergy testing; vaccines; genetic material such as oligonucleotides, DNA, RNA, and plasmids; local anesthetics such as lidocaine and benzocaine; and photosensitizers such as benzoporpherene derivative monoacid ring A (BPD-MA). Other examples include hormones such as adrenaline, testosterone, estrogen, and various pituitary hormones; olfactory agents intended to introduce a pleasing aroma on the skin; antibiotics, such as penicillin, and streptomycine; nitroglycerine for use in connection with cardiac difficulties; psychopharmacological agents; tranquilizers that can be quickly applied by law enforcement agents during the course of apprehending a particularly unwilling suspect; nicotine; analgesics such as acetominophen, ibuprofein and the like; anti-allergy medications; and vitamins and antioxidants that would otherwise be degraded in the digestive tract. Any of these, and other compositions, can be heated before generation of the impulse transient in order to facilitate their transport through the skin.

If the desired composition 36 has a short shelf life, precursors of that composition 36 may be separated into individual compartments 37*a*, 37*b* within the delivery chamber 30 as shown in FIG. 2A. These compartments 37*a*, 37*b* are configured and selected to rupture in response to the impulse transient, thereby spilling their contents into the delivery chamber 30 as shown in FIG. 2B. Once mixed together in the delivery chamber 30, the precursors form the desired composition 36. This design can also be used to deliver compositions that should not be in contact prior to delivery.

Compositions 36 can also include such cosmetic agents such as tattoo inks. For example, a device can be designed to apply a portion of a tattoo image or an entire image in one quick and painless operation. These tattoos would typically be temporary, because the inks are deposited into the epidermis rather than the dermis. In addition, a multiplicity of transdermal delivery devices 10 loaded with inks or coloring agents can cover a substantial portion of the body, thereby providing the ability to subcutaneously change the color of a large portion of the skin to simulate a suntan without the risk of excessive UV exposure.

A multiplicity of transdermal delivery devices 10 having distal caps perforated according to particular designs and loaded with inks of different color can be disposed to cover expanses of skin. When detonated, each transdermal delivery device 10 will imprint on the skin a portion of an image, thereby forming a wearable mosaic on the skin. Because the inks are delivered subcutaneously, the mosaic thus impregnated into the person's skin can last long enough and withstand the environmental stresses associated with a weekend on the beach, during which the wearable mosaic can be suitably displayed. However, since the stratum corneum layer in which the ink is impregnated will eventually slough off, the wearable mosaic can be replaced from time to time.

The use of a luminous component that is invisible under ordinary light but visible in the dark would enable one to "wear" such novelties as a luminous skeleton for Halloween costumes. Different effects can be achieved by providing transdermal delivery devices 10 having delivery chambers 30 loaded with materials that fluoresce when exposed to UV light.

Localization of the composition using the methods and devices of the invention is advantageous because the composition can be delivered with highly localized effects to areas of diseased cells, thereby sparing other tissues of the body. This advantage is particularly apparent when the alternative is to deliver a drug systemically, in which case the drug must be delivered in substantially higher concentrations in order to compensate for dilution in the bloodstream and in which case the drug is apt to reach all internal organs and require metabolization by the liver.

Contents of the Structure: Energetic Material

The detonation chamber 32 contains one or more materials, collectively referred to as energetic material 40, that are selected to detonate or to react in a manner resulting in detonation when exposed to a stimulus of energy.

The energetic material 40 contained within the detonation chamber 32 is selected to generate, upon detonation, an impulse transient having a peak pressure greater than the 350 bar needed to permeabilize the skin. Typically, the peak pressure is, between about 600 and 1000 bar. The peak pressure can be high as about 2000 bar. However, such high pressures are not needed to permeabilize the skin. The range of peak pressure is selected to be sufficient to permeabilize the outermost layer of the epidermis 52, the stratum corneum without causing damage to the viable parts of the skin, such as the dermis and the epidermis.

The energetic material 40 can generate an impulse transient by, for example, rapidly vaporizing upon exposure to an energy stimulus. Alternatively, the energy stimulus may provide the activation energy for a rapid and exothermic chemical reaction. In another embodiment, the energy stimulus may place reactants into proximity so that a spontaneous, rapid and exothermic reaction occurs. Alternatively, the energy stimulus can place reactants into contact with a catalyst that will lower the activation energy sufficiently to allow a spontaneous reaction to occur.

The selection of an energetic material 40 depends on the particular application. Examples of suitable energetic materials include nitrocellulose, glycidyl azide polymer, bis-azidomethyloxetane polymer, azidomethyl methyloxetane polymer and silver azide.

Figure 3A:
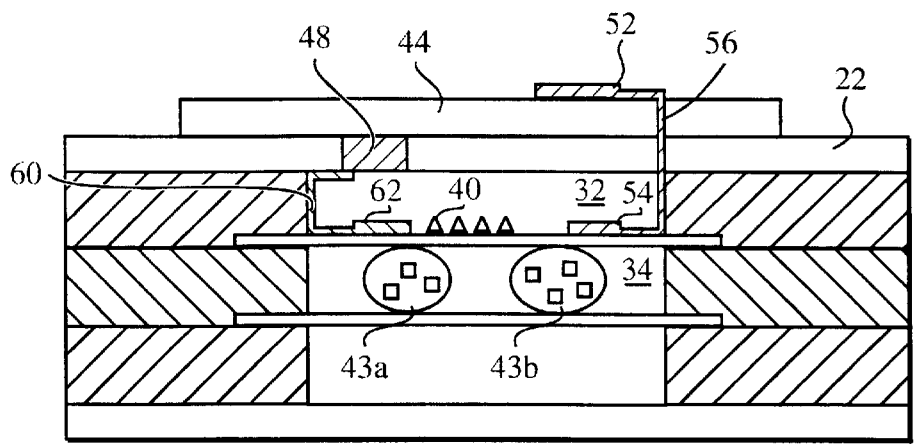
FIG. 3A is a schematic cross-section of a transdermal delivery device in which the expansion material is separated into two compartments and the energetic material is deposited onto the proximal dividing membrane.
Figure 3B:
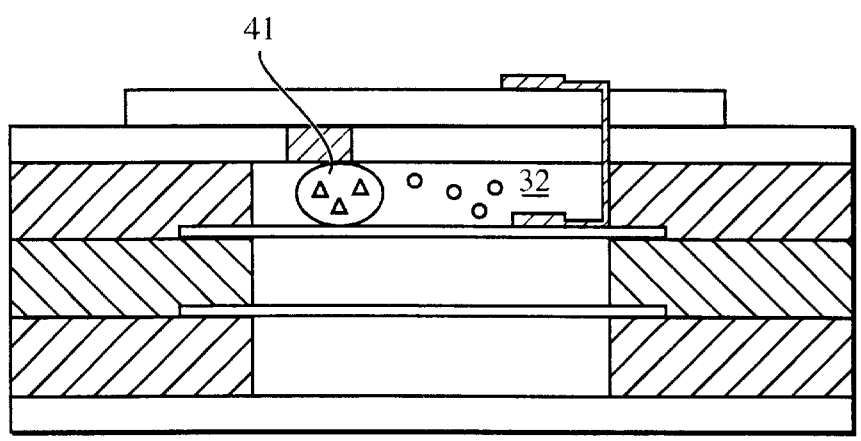
FIG. 3B is a schematic cross-section of a transdermal delivery device in which a precursor of an energetic material is separated into a compartment.
Figure 3C:
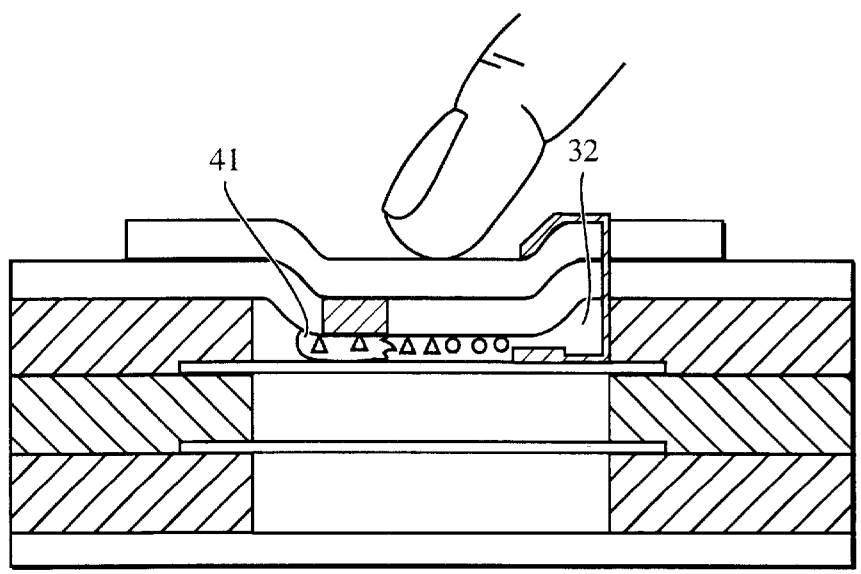
FIG. 3C is a schematic cross-section of the transdermal delivery device of FIG. 3B in which the compartment has been ruptured.

The energetic material 40 can be dispersed throughout the detonation chamber 32 in an optional coupling medium such as a gel, as shown in FIG. 1. Alternatively, the energetic material 40 can be deposited onto the proximal dividing membrane 26 so that the detonation chamber 32 can be used to contain gaseous byproducts of the explosion, as shown in FIG. 3A. In another embodiment, shown in FIG. 3B, a precursor for formation of an explosive material can be contained within a sealed compartment 41 in the detonation chamber 32. The sealed compartment 41 can be ruptured upon the application of an external force, as shown in FIG. 3C. The precursor can then mix with remaining contents in the detonation chamber 32 to form an energetic material 40 that can be detonated upon application of an appropriate stimulus. Alternatively, the precursor can chemically react with remaining contents in the detonation chamber 32 and cause an explosion as a byproduct of the reaction.

Contents of the Structure: Expandable Material

The expansion chamber 34 contains an expandable material 42 selected to expand in volume in response to an explosion in the adjacent detonation chamber 32. The expandable material 42 within the expansion chamber 34 is a material, or a combination of materials, that expands in response to an impulse transient. Precursors to the expandable material can be contained within sealed compartments 43a, 43b in the expansion chamber 34, as shown in FIG. 3A.

These sealed compartments 43a, 43b can be ruptured by the force of an explosion in the detonation chamber 32. The choice of an expandable material 42 depends on the details of the particular application. An expandable material 42 that expands rapidly is useful when the composition in the delivery chamber 30 must be delivered rapidly. An example of a suitable expandable material 42 is a hydrogel formed by rupturing a water bag within the expansion chamber 34 and wetting a hydrogel precursor contained within the expansion chamber 34. Other examples of expandable materials include heparinized polymers, polypeptide elastomers, chitosan poly(ethylene oxide), crosslinked cellulose ethers, and poly(N-isopropylacrylamide).

Detonator

The detonation chamber 32 is coupled to an energy source for providing the energy stimulus required to detonate the energetic material 40 contained within the detonation chamber 32. In the embodiment shown in FIG. 1, this coupling is achieved by a piezoelectric film 44 in electrical communication with the detonation chamber 32. A transdermal delivery device 10 in which a piezoelectric film 44 couples energy into the detonation chamber 32 is particularly advantageous because such a device can be easily activated by a mechanical deformation, for example by squeezing or pressing the piezoelectric film 44.

A distal surface 46 of the piezoelectric film 44 is in electrical communication with a first electrode 48 that penetrates the proximal cap 22. This places the first electrode 46 into contact with the energetic material 40 in the detonation chamber 32. In this configuration, a deformation of the piezoelectric film 44 causes charge to migrate to the distal surface 46. This surface charge then migrates to the surface of the first electrode 48 located inside the detonation chamber 32.

A proximal surface 50 of the piezoelectric film 44 is in electrical communication with a second electrode 52 disposed on the proximal surface 50. This second electrode is, in turn, in electrical communication with a third electrode 54 disposed on the proximal dividing membrane 26 by way of a conducting path 56 that penetrates the proximal cap 22 and travels along an inner surface 58 of the vertical wall 14. The third electrode is thus in electrical contact with the energetic material 40 in the detonation chamber 32. In this configuration, deformation of the piezoelectric layer 44 causes charge to collect on the proximal surface 50 of the piezoelectric film 44. This surface charge in turn migrates to the third electrode 54 by way of the second electrode 52 and the conducting path 54.

In the embodiment shown in FIG. 3A, in which the energetic material 40 is imprinted on the proximal dividing membrane 26, the surface charge generated on the distal surface 46 of the piezoelectric film 44 must be brought into contact with the energetic material 40. This can be achieved, as shown in FIG. 3A, by providing a second conducting path 60 between the first electrode 48 and a fourth electrode 62 disposed on the proximal dividing membrane 26.

In the embodiment shown in FIG. 1, a deformation of the piezoelectric film 44 causes surface charge to collect on the first and third electrodes 48, 54. Depending on the extent of the deformation, this surface charge generates, within the detonation chamber 32, an electric field of sufficient magnitude to cause an electrical discharge within the detonation chamber 32. This discharge triggers detonation of the energetic material 40 in the detonation chamber 32.

Figure 4:
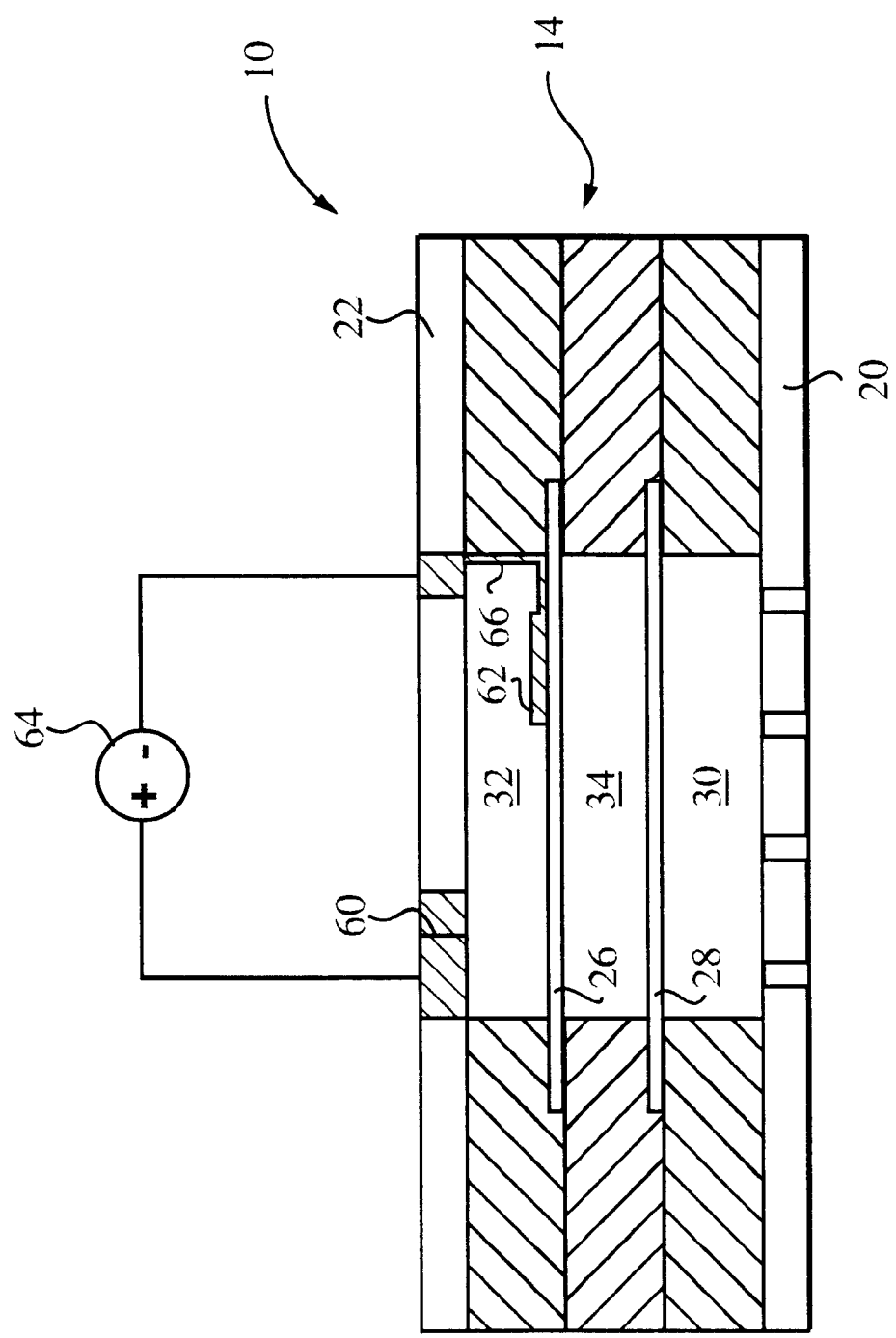
FIG. 4 is a schematic cross-section of a transdermal delivery device connected to a DC voltage source.

As shown in FIG. 4, the detonation chamber 32 can also be coupled to an energy source by placing first and second electrodes 60, 62 in electrical communication with the detonation chamber 32 and connecting the first and second electrodes 60, 62 to a DC voltage source 64. A transdermal delivery device 10 in which the energy source is a DC voltage source 64 is advantageous because the voltage can more readily be controlled and because higher voltages can be generated, thereby ensuring the occurrence of an electrical discharge even when the medium within the detonation chamber 32 has a very high resistivity.

In the embodiment shown in FIG. 4, the DC voltage source 64 generates an electric field within the detonation chamber 32 by causing surface charge to collect on the first and second electrodes 60, 62. The first electrode 60 penetrates the distal cap so that it is in intimate contact with the explosive material 40 in the detonation chamber 32. The second electrode 62 is disposed on the proximal dividing membrane and brought into contact with the DC voltage source 64 by way of a conducting strip 66 on the inside surface 58 of the vertical wall 14. The DC voltage source can be a line-powered DC power supply, e.g. a transformer with a rectifier having suitable ripple cancellation filters, or a battery, such as a NiCad battery, an alkaline battery, a conventional carbon core zinc battery, a lithium battery, or a lead acid battery. By suitable choice of voltage, the electric field can be made of sufficient magnitude to cause an electrical discharge within the detonation chamber 32. This discharge triggers detonation of the energetic material 40 in the detonation chamber 32.

Other energy sources can also be used to detonate an explosion in the detonation chamber 32. For example, a catalyst moved into contact with the energetic material 40 can be used to detonate the explosion. Alternatively, the detonation chamber 32 can include reactants that are brought together so as to initiate a reaction that ultimately results in an explosion. The reactants may, for example, occupy two regions within the detonation chamber 32 that are separated by an easily ruptured membrane, as shown in FIGS. 3B and 3C. Another mechanism for detonating the energetic material 40 is to locally apply heat to the material. This can be achieved by applying a heat source to the energetic material. Examples of such heat sources include hot water bottles, electric heat pads, heat pads powered by an exothermic reaction caused by bringing reactants into contact, e.g. by breaking membranes separating the reactants, the body heat from a hand, solar heat, augmented perhaps by a suitable lens or magnifying glass, heat from a match held in proximity to the device, or a fuse lit by a flame.

Method of Manufacture

Referring again to FIG. 1, the transdermal delivery device 10 as described herein can be manufactured by gluing a first rubber washer 67a to a distal cap 20 so that the inner surface of the first rubber washer 67a forms a wall for the delivery chamber 30 and the distal cap 20 forms a floor of the delivery chamber 30. The delivery chamber 30 is then filled with a suitable composition 36 and covered with the distal dividing membrane 28. A second rubber washer 67b is then glued onto the first rubber washer 67a so that the first and second rubber washers hold between them the distal dividing membrane 28. A suitable adhesive for use in assembly of the device 10 is an epoxy. However, other adhesives, e.g. rubber cement, silicone, urethane, UV cured adhesives, cyanoacrylates, or other acrylic based adhesives can be used.

The inner surface of the second rubber washer 67b forms the wall of the expansion chamber 34 and the distal dividing membrane 28 forms the floor of the expansion chamber 34. The expansion chamber 34 is then filled with the expandable material 42 or with structures that contain precursors of the expandable material 42. Once this is done, the proximal dividing membrane 26 is placed over the expansion chamber 34 and a third rubber washer 67c is glued onto the second rubber washer 67b so that the second and third washers hold between them the proximal dividing membrane 26. The inner surface of the third washer 67a and the proximal dividing membrane 26 now form the wall and floor of the detonation chamber 32. The stacked first, second, and third washers together form the vertical wall 14 of the transdermal delivery device 10.

The next step in the manufacture of the transdermal delivery device 10 is to imprint electrical connections on the wall of the detonation chamber 32, so as to form the conducting path 56, and on the proximal surface of the proximal dividing membrane 26, so as to form the third electrode 54. This is most easily accomplished by stenciling conductive paint on those surfaces.

Once the electrical connections are in place, the energetic material is placed in the detonation chamber 32 and the proximal cap 22 is glued onto the third washer 67c. The first electrode 48 is then inserted through the proximal cap 22 and a piezoelectric material is glued onto the proximal cap 22. The second electrode 52 and the remainder of the conducting path 56 is then stenciled onto the proximal cap 22.

The Impulse Transient

An impulse transient generated by an explosion in the detonation chamber 32 has a peak pressure that is sufficient to permeabilize the skin but not sufficient to cause skin damage. The numerical quantities will depend on what portion of the skin is to be permeabilized. To permeabilize most areas of skin covered by the stratum corneum, this peak pressure is more than about 400 bar, which is the approximate threshold for permeabilizing the stratum corneum, and less than about 1800 to 2000 bar. Preferably, the pressure is approximately 1000 bar. For skin covered by a mucosal layer, the peak pressure required is considerably lower. For permeabilizing epithelial mucosal layers, the preferred peak pressure is between about 300 and 600 bar.

Figure 5:
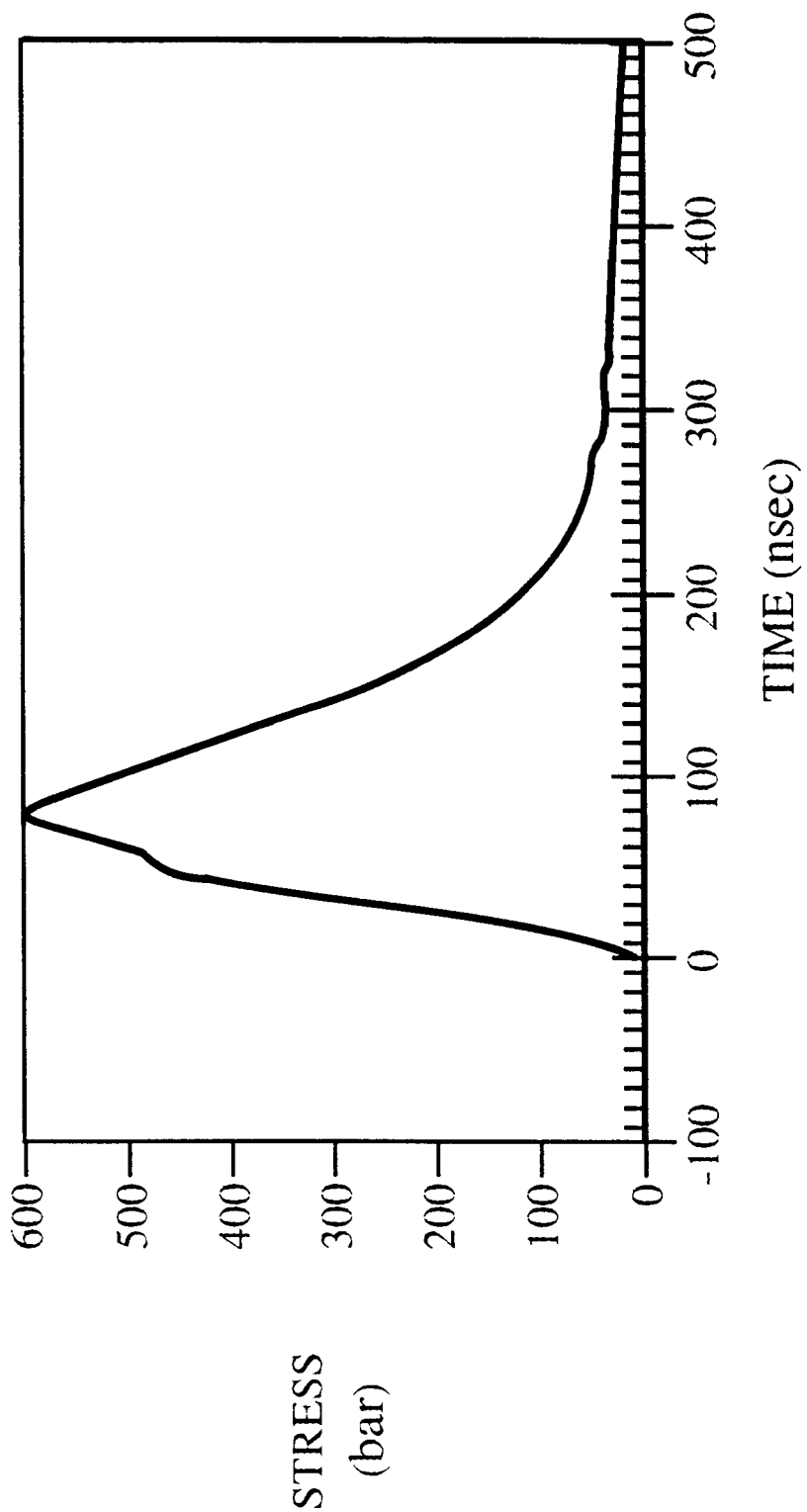
FIG. 5 is an impulse transient generated by an explosion in the detonation chamber of the device shown in FIG. 1.

The impulse transient generated by the explosion is not a shock wave but a pulse having a finite rise time on the order of 200 nanoseconds or less. The preferred duration of the impulse transient is generally between 100 nanoseconds and 1100 nanoseconds. FIG. 5 shows waveform for a typical impulse transient.

Operation of the Transdermal Delivery Device

In operation, the housing 24 of the transdermal delivery device 10 rests with its distal cap 20 in contact with the skin 68. Because the delivery interval for most compositions 36 is brief, the housing 24 can simply be held on the skin by the patient during the delivery interval. Alternatively, the housing 24 can be strapped onto the skin 68, e.g., using adhesive tape or a hook and loop fastening tape. In an optional feature of the invention, the adhesive can be applied to the portion of the housing 24 that is to contact the skin 68. This adhesive can be protected during storage by a plastic sheet that is peeled off and discarded prior to use of the transdermal delivery device 10.

With the distal cap 20 resting securely on or against the skin 68, the energetic material 40 is detonated using one of the methods described herein. For example, in the embodiment of FIG. 1, the patient presses the piezoelectric layer 44 to generate an electrical discharge. In the embodiment of FIG. 4, the DC voltage source 64 is activated.

The explosion within the detonation chamber 32 generates an impulse transient that propagates through the expansion and delivery chambers 34, 30 until it reaches the skin 68. At the skin 68, the impulse transient interacts with the outermost layer, the stratum corneum, so as to significantly increase its permeability. One or more surfactants, if included in the composition 36, can delay the stratum corneum's recovery of its impermeability, thereby extending the delivery interval during which transdermal delivery of the composition 36 is possible.

Figure 6:
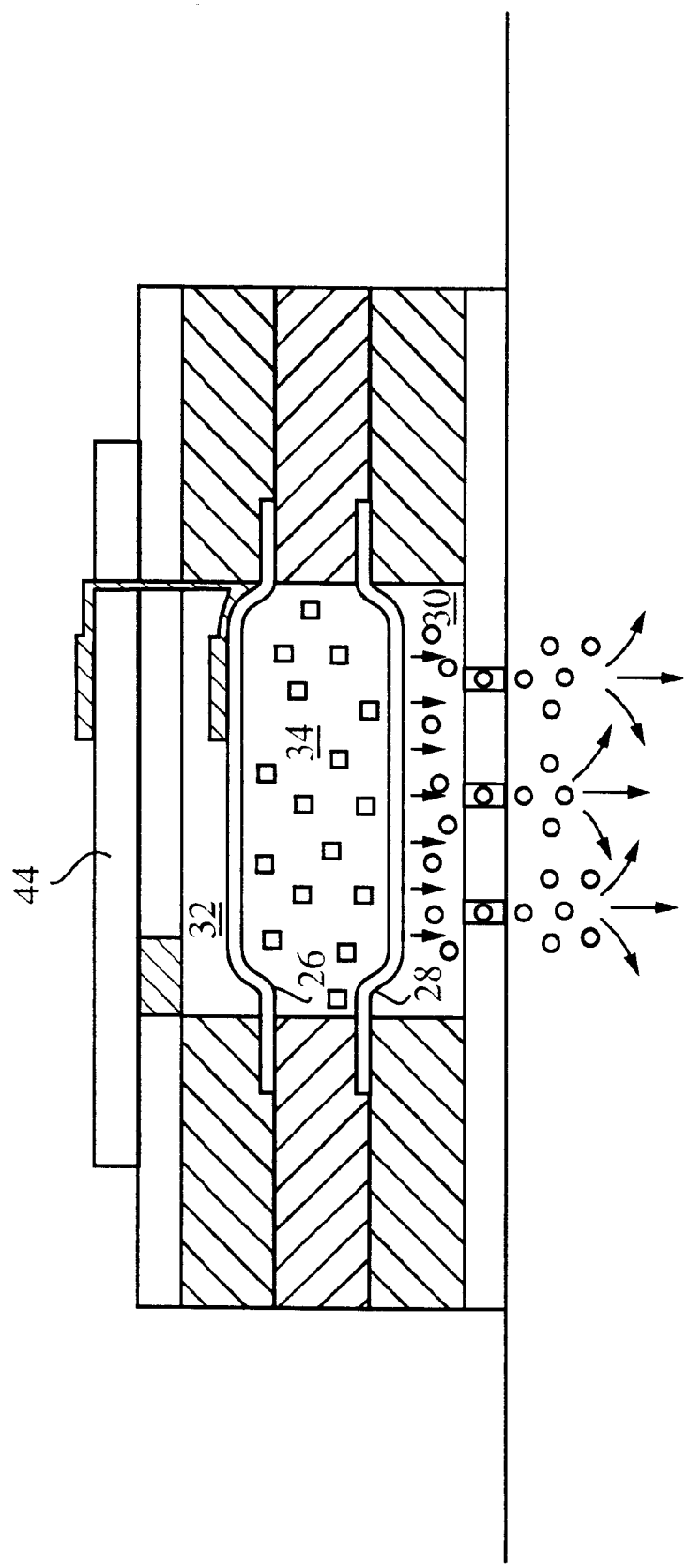
FIG. 6 is a schematic cross-section of the transdermal delivery device of FIG. 1 following detonation.

As it propagates through the expansion chamber 34, the impulse transient generated by the explosion also interacts with the expandable material 42 contained therein. In response to this interaction, the expandable material 42 expands in volume. This expansion in the volume of the expandable material 42 causes the distal dividing membrane 28 to deform and move distally toward the epidermis 52 as seen in FIG. 6. The distal dividing membrane 28 thus acts as a plunger exerting a distally directed pressure on the composition 36 contained within the detonation chamber 32. This distally directed pressure forces the composition 36 to move through perforations in the distal cap 20 and through the stratum corneum, which, as noted earlier, has been made temporarily permeable by the impulse transient.

It is apparent from the foregoing description that the transdermal delivery device 10 provides two modes for transdermal delivery of a composition. Once the stress wave generated by the explosion permeabilizes the stratum corneum, the composition 36 diffuses through the epidermis as a result of the concentration gradient. For certain applications, as described below in connection with FIG. 7, this mode is adequate.

Concurrently, the expansion of the expandable material 42 in the expansion chamber 34 drives the distal membrane 28 in the distal direction. This provides a motive force that increases the rate at which the composition 36 passes through the stratum corneum. As a result of the force generated by the expansion, the transdermal delivery device 10 propels the composition 36 into the skin with a high sustained transdermal flow rate thereby allowing more of the composition 36 to flow across the skin during the delivery interval.

In addition to its enhanced performance, the transdermal delivery device 10 eliminates the need for complex and costly power sources associated with the operation of conventional active transdermal delivery systems. For example, the new transdermal delivery device requires no ultrasound generator or a laser. At most, the transdermal delivery device 10 requires a simple and inexpensive DC voltage source 50, as shown in FIG. 4. In the embodiment shown in FIG. 1, the transdermal deliver device 10 needs no external energy source other than a force exerted on the piezoelectric film 44.

Figure 7:
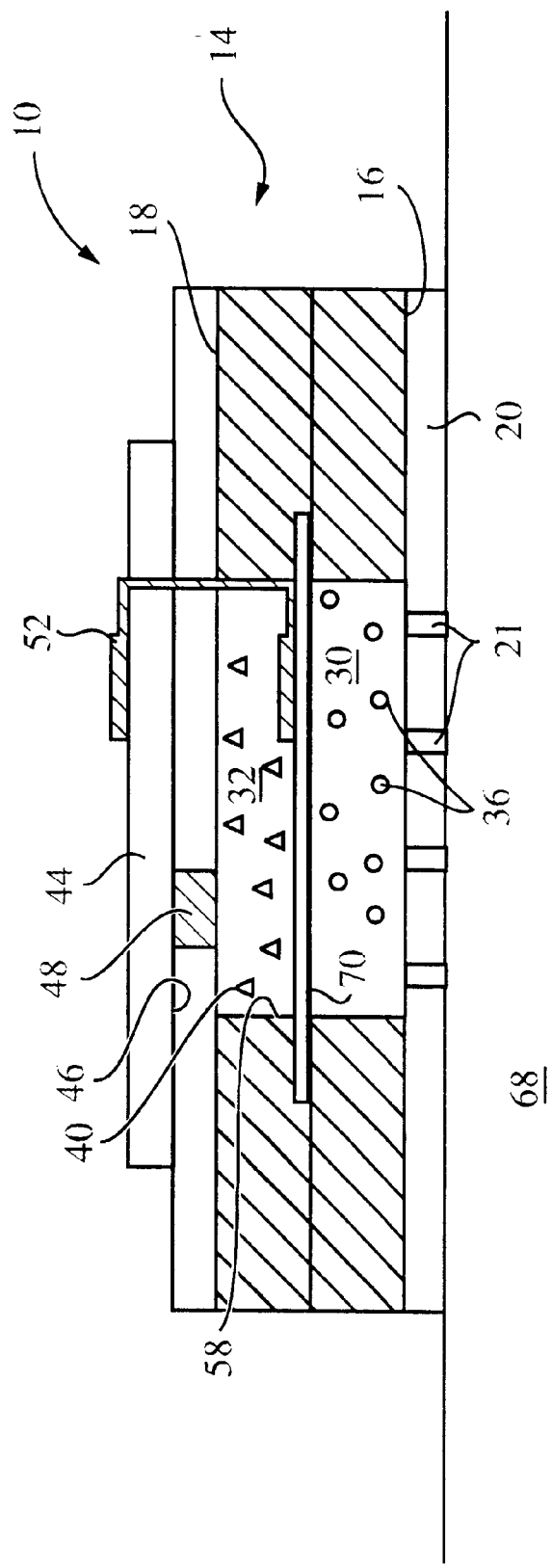
FIG. 7 is a schematic cross-section of a transdermal delivery device having only two layers.

In an alternative embodiment, shown in FIG. 7, a single dividing membrane 70 divides the interior volume enclosed by the housing 24 into a delivery chamber 30 and a detonation chamber 32. This embodiment is thus identical to the embodiment described in FIG. 1 except that there is no expansion chamber and hence, in operation, there is no force exerted on the composition 36 to drive it through the skin 68. The embodiment of FIG. 7 is thus a passive delivery device.

In operation, the energetic material 40 is detonated in the same manner as described in connection with the embodiment of FIG. 1. The resulting impulse transient begins a delivery interval during which the skin 68 is permeable to the composition 36. The composition 36 then diffuses into the skin 68 at a rate proportional to the concentration gradient across the skin 68.

The advantage of the embodiment shown in FIG. 7 is that the energetic material 40 is separated from the composition 36. As a result, it is less likely, in this embodiment, that the constituents of the composition will be adversely affected by the brief, but intense, heat flash generated during the explosion of the energetic material 40.

Figure 8:
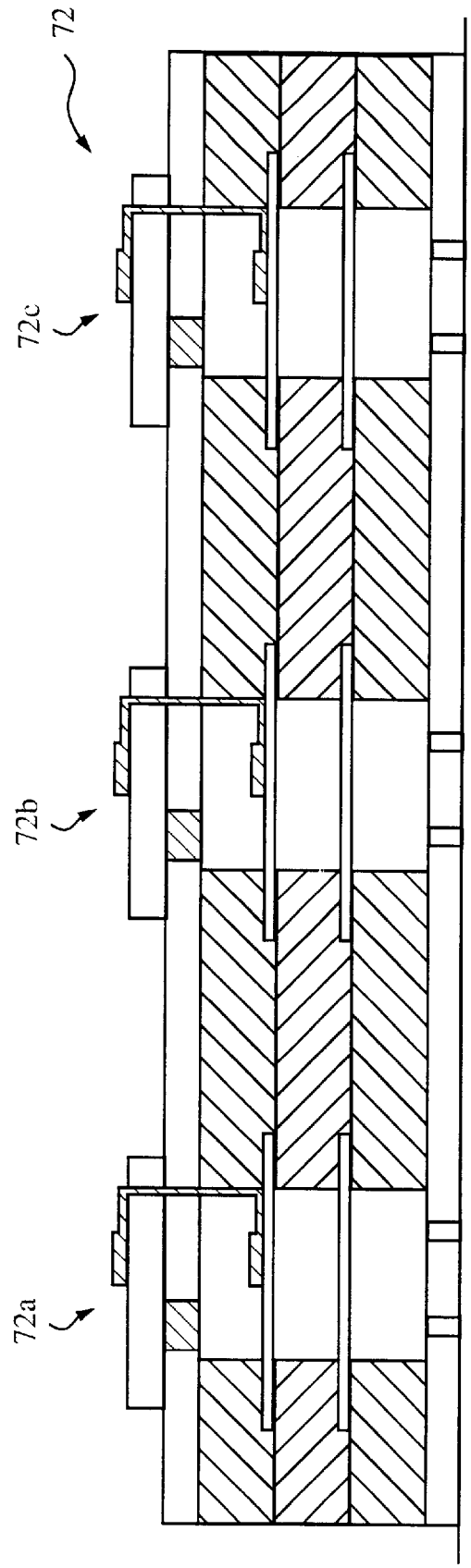
FIG. 8 is a schematic cross-section of a multi-element transdermal delivery device.

In another embodiment, shown in FIG. 8, a multi-element transdermal delivery device 72 is made up of several transdermal delivery devices 72a, 72b, 72c as described above, or one device with several chambers, each of which is independently detonated. A multi-element transdermal delivery device 72 is useful when several doses of the composition 36 are required at different times or when several different compositions are to be adminstered at substantially the same time. Alternatively, the dosage may be so high that the cross-sectional area required for a single housing 24 would be very large. Under these circumstances, the excessive overpressure of the explosion required to deliver the entire composition 36 may compromise the patient's safety. The multi-element transdermal delivery device 72 may also be indicated when the composition 36 includes molecules that penetrate the skin very slowly, in which case not enough composition can penetrate the skin during the limited delivery time associated with a single explosion.

OTHER EMBODIMENTS

It is to be understood that while the foregoing detailed description has described selected embodiments of the invention, it is intended to illustrate and not to limit the scope of the invention. The invention, together with other aspects, advantages, and modifications thereof, are limited only by the scope of the appended claims.

What is claimed is:

1. A device for transdermal delivery of a composition, the device comprising:
   a delivery chamber arranged to contain the composition; and
   a detonation chamber arranged to contain an energetic material;
   a first dividing membrane between the delivery chamber and the detonation chamber; and
   a detonator that causes the energetic material to explode, thereby initiating an impulse transient that passes from the detonation chamber, through the delivery chamber, and out of the transdermal delivery device.

2. The device of claim 1, further comprising an expansion chamber arranged between the delivery chamber and the detonation chamber, and a second dividing membrane between the expansion chamber and the detonation chamber.

3. The device of claim 1, wherein the delivery chamber and the detonation chamber are substantially parallel layers.

4. The device of claim 2, wherein the delivery chamber, the detonation chamber, and the expansion chamber are substantially parallel layers.

5. The device of claim 1, wherein the detonator comprises a piezoelectric film in electrical communication with the energetic material in the detonation chamber.

6. The device of claim 1, wherein the detonator comprises an electrode for connecting to a DC voltage source, the electrode being in electrical communication with the energetic material in the detonation chamber.

7. The device of claim 1, wherein the detonator comprises a DC voltage source and an electrode for connecting the DC voltage source to the energetic material in the detonation chamber.

8. The device of claim 2, wherein the expansion chamber contains an expansion material selected to increase in volume in response to the impulse transient.

9. The device of claim 8, wherein the expansion material is a hydrogel.

10. The device of claim 2, wherein the expansion chamber contains precursors to an expansion material, the precursors forming the expansion material in response to the impulse transient.

11. The device of claim 10, wherein the expansion chamber contains a first compartment containing a first precursor and a second compartment containing a second precursor and the first and second compartment are configured to rupture in response to the impulse transient, thereby allowing mixing of the first and second precursors to form the expansion material.

12. The device of claim 1, wherein the delivery chamber contains a surfactant.

13. The device of claim 12, wherein the surfactant is selected from the group consisting of sodium lauryl sulfate, benzalkonium chloride, and cocoamidopropyl betaine.

14. The device of claim 1, wherein the delivery chamber contains a composition that includes a pharmaceutical agent.

15. The device of claim 14, wherein the pharmaceutical agent is selected from the group consisting of a protein, a nucleic acid, a local anesthetic, and a photosensitizer.

16. The device of claim 1, wherein the delivery chamber contains a composition that includes a cosmetic agent.

17. The device of claim 1, wherein the delivery chamber contains precursors to the composition, the precursors forming the composition in response to the impulse transient.

18. The device of claim 1, wherein the delivery chamber contains a first compartment containing a first precursor and a second compartment containing a second precursor and the first and second compartment are configured to rupture in response to the impulse transient, thereby allowing mixing of the first and second precursors to form the composition.

19. The device of claim 1, wherein the detonation chamber contains an energetic material selected to generate an impulse transient having a peak pressure in excess of 350 bar.

20. The device of claim 19, wherein the energetic material is selected to generate an impulse transient having a peak overpressure in the range between approximately 600 bar and approximately 800 bar.

21. The device of claim 1, wherein the detonation chamber contains an energetic material selected from the group consisting of nitrocellulose, glycidyl azide polymer, bis-azidomethyloxetane polymer, azidomethyl methyloxetane polymer, and silver azide.

22. The device of claim 1, wherein the detonation chamber is filled with a medium that contains an energetic material.

23. The device of claim 1, wherein the energetic material is deposited on the first dividing membrane.

24. The device of claim 1, wherein the detonation chamber contains precursors to the energetic material, the precursors being configured to form the energetic material in response to the detonating stimulus.

25. The device of claim 1, wherein the detonation chamber contains a first compartment containing a first precursor and a second compartment containing a second precursor and the first and second compartment are configured to rupture in response to the detonating stimulus, thereby allowing mixing of the first and second precursors to form the energetic material.

26. The device of claim 1, wherein the first dividing membrane is made from a material selected from the group consisting of mylar and polyethylene.

27. The device of claim 2, wherein the second dividing membrane is made from a material selected from the group consisting of mylar and polyethylene.

28. The device of claim 2, wherein the second dividing membrane is selected to be deformable in response to the impulse transient.

29. The device of claim 1, wherein the first dividing membrane is selected to provide an impedance match between the delivery chamber and the detonation chamber.

* * * * *